(12) United States Patent
Son et al.

(10) Patent No.: US 10,881,854 B2
(45) Date of Patent: Jan. 5, 2021

(54) RESPIRATORY MUSCLE STRENGTHENING DEVICE

(71) Applicant: RESEARCH COOPERATION FOUNDATION OF YEUNGNAM UNIVERSITY, Gyeongsan-si (KR)

(72) Inventors: Su Min Son, Daegu (KR); Eun Yong Choi, Daegu (KR); Joon Ha Lee, Daegu (KR); So Young Kwak, Daegu (KR)

(73) Assignee: RESEARCH COOPERATION FOUNDATION OF YEUNGNAM UNIVERSITY, Gyeongsan-si (KR)

(*) Notice: Subject to any disclaimer, the term of this patent is extended or adjusted under 35 U.S.C. 154(b) by 118 days.

(21) Appl. No.: 16/315,163

(22) PCT Filed: Jun. 20, 2017

(86) PCT No.: PCT/KR2017/006480
§ 371 (c)(1),
(2) Date: Jan. 4, 2019

(87) PCT Pub. No.: WO2018/079974
PCT Pub. Date: May 3, 2018

(65) Prior Publication Data
US 2020/0179686 A1  Jun. 11, 2020

(30) Foreign Application Priority Data

Oct. 28, 2016 (KR) .................. 10-2016-0142066

(51) Int. Cl.
*A61N 1/36* (2006.01)
*A61N 1/04* (2006.01)

(52) U.S. Cl.
CPC ......... *A61N 1/3601* (2013.01); *A61N 1/0452* (2013.01); *A61N 1/0492* (2013.01); *A61N 1/36031* (2017.08)

(58) Field of Classification Search
CPC .............. A61N 1/3601; A61N 1/36031; A61N 1/0452; A61N 1/0492
See application file for complete search history.

(56) References Cited

U.S. PATENT DOCUMENTS

| 5,134,995 A | 8/1992 | Gruenke et al. |
| 5,911,218 A | 6/1999 | DiMarco |

(Continued)

FOREIGN PATENT DOCUMENTS

| JP | 2000-116784 A | 4/2000 |
| JP | 2001-523127 A | 11/2001 |

(Continued)

OTHER PUBLICATIONS

International Search Report for PCT/KR2017/006480 dated Oct. 13, 2017 from Korean Intellectual Property Office.

*Primary Examiner* — Paula J Stice
(74) *Attorney, Agent, or Firm* — Revolution IP, PLLC

(57) ABSTRACT

Provided is a respiratory muscle strengthening device, in which an inhalation start signal is generated correspondingly at an inhalation start time when a patient inhales air or an exhalation start signal is generated correspondingly at an exhalation start time when the patient exhales air, an electric signal according to the inhalation start signal or the exhalation start signal is transmitted to an electric muscle stimulator via a communication unit, a muscle pad installed on respiratory muscles of the patient enables smooth breathing motion by stimulating the respiratory muscles based on a signal transmitted from the electric muscle stimulator, and a receptor pad is provided to the respiratory muscles such that an alarm of determining whether electric stimulation is (Continued)

normally applied via the state of the respiratory muscles detected through the receptor pad is output, thereby securing reliability of a device.

7 Claims, 4 Drawing Sheets

(56) References Cited

U.S. PATENT DOCUMENTS

| | | | |
|---|---|---|---|
| 6,360,740 | B1 | 3/2002 | Ward et al. |
| 2005/0021102 | A1* | 1/2005 | Ignagni ................ A61N 1/3601 607/42 |
| 2009/0012573 | A1 | 1/2009 | Karell |
| 2011/0313332 | A1 | 12/2011 | Rahman et al. |
| 2015/0045848 | A1* | 2/2015 | Cho ..................... A61B 5/0809 607/18 |
| 2016/0158092 | A1 | 6/2016 | Amblard et al. |

FOREIGN PATENT DOCUMENTS

| | | |
|---|---|---|
| JP | 6004095 B2 | 10/2016 |
| KR | 10-0451322 B1 | 10/2004 |
| KR | 10-0743354 B1 | 7/2007 |
| KR | 10-1138958 B1 | 4/2012 |
| KR | 10-2014-0051570 A | 5/2014 |
| KR | 10-1572761 B1 | 11/2015 |
| KR | 10-1647892 B1 | 8/2016 |
| WO | 92-11054 A1 | 7/1992 |

* cited by examiner

RESPIRATORY MUSCLE STRENGTHENING DEVICE

TECHNICAL FIELD

The present disclosure relates to a respiratory muscle strengthening device, and more particularly, to a respiratory muscle strengthening device, in which an inhalation start signal is generated correspondingly at an inhalation start time when a patient inhales air or an exhalation start signal is generated correspondingly at an exhalation start time when the patient exhales air through a spontaneous breathing signal of the patent or an artificial respirator, an electric signal according to the inhalation start signal or the exhalation start signal is transmitted to an electric muscle stimulator via a communication unit, a muscle pad installed on respiratory muscles enables smooth breathing motion by stimulating the respiratory muscles based on a signal transmitted from the electric muscle stimulator, and a muscle pad internal or external type receptor pad is provided to the respiratory muscles such that the receptor pad detects a state (muscle contraction and relaxation movement degrees, movement time, or the like) of the respiratory muscles to determine normal application of electric stimulation via the state of the respiratory muscles detected through the receptor pad, thereby securing reliability of a device.

BACKGROUND ART

Mechanical respiration using an artificial respirator is a respiratory method inevitably applied to patients having acute respiratory distress syndrome who are unable to breath by themselves.

Unlike using respiratory muscles normally, such a respiratory method maintains respiration by artificially injecting air using an artificial respirator in accordance with a certain condition, and thus when the respiratory method is used for a long period of time, the respiratory muscles are prone to be in a deconditioning state as a patient no longer uses his/her own respiratory muscles, and accordingly, strengthening exercise of the respiratory muscles is again necessitated after a respiratory disease is cured and also, a respirator weaning period itself may be delayed.

KR 10-2014-0051570 (published on May 2, 2014) discloses an artificial respirator that optimizes exhaustion and inhalation according to structural characteristics of patient's alveoli to provide a large amount of mixed gas to the patient with a small respiration amount, and a method for controlling the same, wherein the artificial respirator includes an inhalation adjusting valve for supplying the mixed gas to the patient's lungs by adjusting a flow rate and pressure of the mixed gas provided to the patient, a positive endexpiratory pressure valve for externally discharging a discharge gas by adjusting a flow rate and pressure of the discharge gas discharged from the patient's lungs, and a control module for generating an operation signal corresponding to a high frequency respiratory mode based on biometric data about the structural characteristics of the patient's alveoli and providing the generated operation signal to the inhalation adjusting valve and the positive endexpiratory pressure valve. According to the disclosed technology, the operation signal, which has a respiration amount of smaller amplitude than a preset respiration amount of amplitude for a common person and has a shorter high frequency respiration period than the respiration period of the common person, is generated based on the biometric data about the structural characteristics of the alveolus to control the inhalation adjusting valve and the positive endexpiratory pressure valve to supply the mixed gas required by the patient such that the circulation of the lungs, which is the exchange of oxygen and carbon dioxide in the mixed gas, is generated without expanding or reducing the alveoli. Accordingly, the circulation efficiency of the alveoli may be improved, and since the patient is provided with high frequency respiration without separated additional devices, the respirator has a simple structure and thus production processes and costs may be reduced and durability and reliability of the product are further improved.

KR 10-1138958 (registered on Apr. 16, 2012) discloses a flow velocity direction control device of an artificial respiratory machine, which provides the artificial respiratory machine having a simple structure and thus movable, supplies only a required flow velocity to a patient, is applicable to a critical patient by increasing an inhalation and exhalation velocity, provides an oxygen therapy function as oxygen concentration corresponding to a patient supplied air flow velocity is precisely controlled, and reduces unnecessary oxygen consumption by controlling the oxygen concentration, thereby securing stability of a device.

According to the disclosed related art, there is provided a pneumatic control device including a bypass filter that is installed to face a flow velocity direction of discharged air discharged through a blower and controls the discharged air to be externally discharged based on the flow velocity and pressure during inhalation and exhalation of the patient, and thus a response speed with respect to the inhalation and exhalation of the air provided to the patient is increased and the oxygen concentration corresponding to the flow velocity of the air supplied to the patient is supplied. Accordingly, the pneumatic control device is applicable to the critical patient and an intubation type.

As described above, in the related art, most patient suffering from acute respiratory distress syndrome are subjected to artificial mechanical ventilation using a respirator in a intensive care unit, and it is well known that, in this case, it takes a large amount of time for most of the patients to recover a respiratory function after a respiratory disease is cured while attempting respirator weaning due to deconditioning of the respiratory muscles.

Such deconditioning of the respiratory muscles is the most common cause of prolonged or failed respirator weaning, and accordingly, prevalence of ventilator-induced pneumonia may be increased.

When the general artificial respirator as described above is used, exercise for strengthening the respiratory muscles is again necessitated after the respiratory disease is medically cured, and consequent manpower, time, and economical costs for additional treatment are generated.

In order to overcome such issues, KR 10-1572761 (registered on Nov. 23, 2015) provides a respiratory muscle strengthening device including an artificial respirator for generating an inhalation start signal correspondingly at an inhalation start time when a patient inhales air or generating an exhalation start signal correspondingly at an exhalation start time when the patient exhales air, and transmitting the inhalation start signal or exhalation start signal wirelessly or via wire, and an electric neuromuscle stimulator installed on respiratory muscles of the patient and stimulates corresponding respiratory muscles upon receiving the inhalation start signal or the exhalation start signal from the artificial respirator wirelessly or via wires.

However, in such a general respiratory muscle strengthening device, it is difficult to monitor whether a correct signal is applied to the respiratory muscles according to a respiratory time and whether the respiratory muscles are moved correctly according to the signal, and thus a subject would express inconvenience about breathing motion.

DESCRIPTION OF EMBODIMENTS

Technical Problem

Provided is a respiratory muscle strengthening device, in which an inhalation start signal is generated correspondingly at an inhalation start time when a patient inhales air or an exhalation start signal is generated correspondingly at an exhalation start time when the patient exhales air through spontaneous breathing of the patent or an artificial respirator, an electric signal according to the inhalation start signal or the exhalation start signal is transmitted to an electric muscle stimulator via a communication unit, a muscle pad installed on respiratory muscles of the patient enables smooth breathing motion by stimulating the respiratory muscles based on a signal transmitted from the electric muscle stimulator, and a muscle pad internal or external type receptor pad is provided to the respiratory muscles such that the receptor pad detects a state of the respiratory muscles and outputs an alarm when the state of the respiratory muscles, which do not satisfy pre-setting, is detected, thereby securing reliability of a device.

Solution to Problem

According to an aspect of the present disclosure, a respiratory muscle strengthening device includes: an electric muscle stimulator installed on respiratory muscles of a patient and stimulating the respiratory muscles based on spontaneous breathing of a patient or external inhalation start signal or exhalation start signal; and a receptor pad installed on the respiratory muscles of the patient and detecting a state of the respiratory muscles.

The electric muscle stimulator may contract the respiratory muscles in accordance with the spontaneous breathing of the patient or an inhalation or exhalation signal detected from the outside according to a ratio of inhalation to exhalation or pre-set an electric stimulating time of the respiratory muscles corresponding to the contraction, contract inhalation muscles among the respiratory muscles for an inhalation muscle electric stimulating time when the inhalation start signal is received, and contract exhalation muscles among the respiratory muscles for an exhalation muscle electric stimulating time when the exhalation start signal is received.

The electric muscle stimulator may contract the respiratory muscles in accordance with the spontaneous breathing of the patient or an inhalation or exhalation signal detected from the outside according to the inhalation start signal or the exhalation start signal or pre-set stimulation strength for each region of the respiratory muscles corresponding to the contraction, and stimulate each region of the respiratory muscles by adjusting a stimulation degree of each region to the pre-set stimulation strength.

When necessary, the respiratory muscles may be stimulated upon receiving the signal according to a respiratory condition set in an artificial respirator.

The electric muscle stimulator may include: a communication unit for inverse-converting the spontaneous breathing of the patient or a respiratory stimulation signal applied from the outside to the inhalation start signal or the exhalation start signal; an operation control unit for generating a first driving control signal or a second driving control signal correspondingly to the inhalation start signal or the exhalation start signal obtained by the communication unit; a memory unit for storing a program and data necessary for driving control of the operation control unit; a plurality of inhalation muscle pads pre-attached respectively to inhalation muscles among the respiratory muscles of the patient and stimulating a corresponding inhalation muscle according to the first driving control signal generated by the operation control unit; and a plurality of exhalation muscle pads pre-attached respectively to exhalation muscles among the respiratory muscles of the patient and stimulating a corresponding exhalation muscle according to the second driving control signal generated by the operation control unit.

The receptor pad may be attached around each of the plurality of inhalation muscle pads or each of the plurality of exhalation muscle pads separately from the plurality of inhalation muscle pads or the plurality of exhalation muscle pads to detect a motion degree of the respiratory muscles.

The receptor pad may be attached to the inhalation muscles or the exhalation muscles by the plurality of inhalation muscle pads or the plurality of exhalation muscle pads by being integrated with the plurality of inhalation muscle pads or the plurality of exhalation muscle pads to detect a motion degree of the respiratory muscles.

The operation control unit may determine electric stimulation output through the plurality of inhalation muscle pads or the plurality of exhalation muscle pads, and whether the electric stimulation is normally applied via the state of the respiratory muscles detected through the receptor pad.

The respiratory muscle strengthening device may further include an alarm unit generating alarm sound to a user when the operation control unit determines that the electric stimulation is not normally applied.

The respiratory muscle strengthening device may further include a respiration detecting unit generating the inhalation start signal correspondingly at an inhalation start time when the patient inhales air or generating the exhalation start signal correspondingly at an exhalation start time when the patient exhales air, and transmitting the inhalation start signal or the exhalation start signal to the electric muscle stimulator.

Advantageous Effects of Disclosure

A respiratory muscle strengthening device according to an embodiment of the present disclosure has following effects.

First, by continuously using respiratory muscles even while an artificial respirator is used, the respiratory muscles can be used while simultaneously curing a respiratory disease, and accordingly, manpower, time, and economical costs of additional treatment for respiratory muscle strengthening exercise performed again after the respiratory disease is medically cured can be reduced, and not only the respiratory muscles are strengthened, but also early respirator weaning is induced.

Second, by performing strengthening exercise of the respiratory muscles through a pad attached to the respiratory muscles by using an electric neuromuscle stimulator, a method of use is simple, an additional space or equipment is not required, synergy is generated with respect to respiration, and the respiratory muscles are continuously strengthened, and thus the respirator weaning can be advanced.

Third, by further providing a receptor pad to the respiratory muscles, the receptor pad detects a state (muscle contraction and relaxation movement degrees, movement time, or the like) of the respiratory muscles, and normal application of electric stimulation is determined via the state of the respiratory muscles detected through the receptor pad and an alarm is output when a normal range is exceeded, and thus reliability of a device can be secured.

BEST MODE

Figure 1:
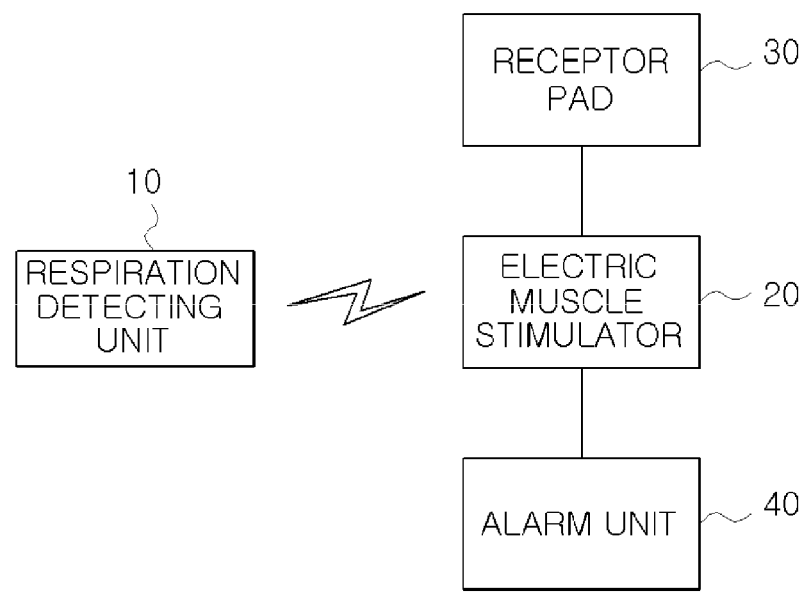
FIG. 1 is an exemplary diagram of a respiratory muscle strengthening device according to an embodiment of the present disclosure.
Figure 2:
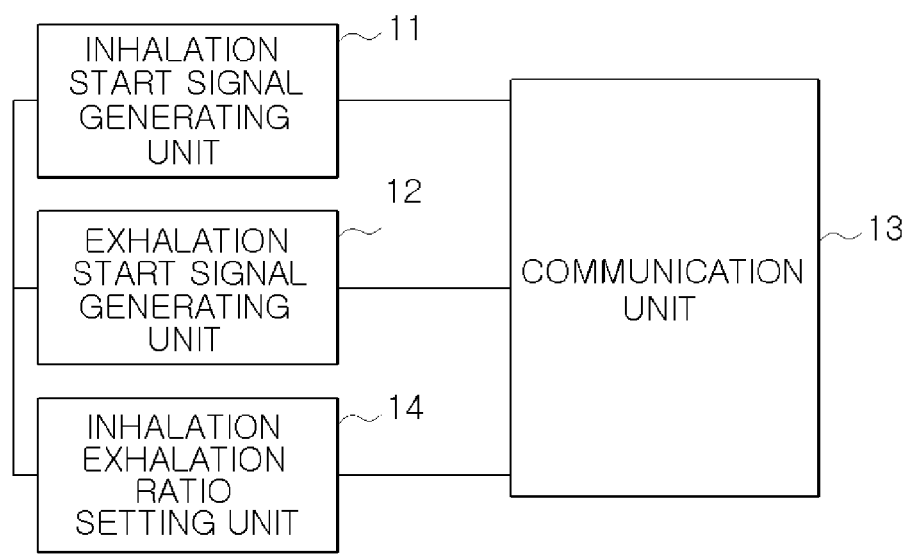
FIG. 2 is an exemplary diagram of a respiration detecting unit according to an embodiment of the present disclosure.

According to the present disclosure, an inhalation start signal is generated correspondingly at an inhalation start time when a patient inhales air or an exhalation start signal is generated correspondingly at an exhalation start time when the patient exhales air, an electric signal according to the inhalation start signal or the exhalation start signal is transmitted to an electric muscle stimulator via a communication unit, a muscle pad installed on respiratory muscles of the patient enables smooth breathing motion by stimulating the respiratory muscles based on a signal transmitted from the electric muscle stimulator, and a receptor pad is further provided to the respiratory muscles such that normal application of electric stimulation is determined via the state of the respiratory muscles detected through the receptor pad, thereby securing reliability of a device.

MODE OF DISCLOSURE

Hereinafter, the present disclosure will be described more fully with reference to the accompanying drawings, in which exemplary embodiments of the disclosure are shown. The terms or words used herein must not be interpreted in their common or dictionary definitions, but must be interpreted in the meanings and concept corresponding to the aspect of the present disclosure, based on the principle that the inventor(s) can suitably define the concept of terms in order to describe the disclosure in the best manner.

Accordingly, the embodiments and drawings described herein are only preferred examples, and do not represent the technical aspects of the present disclosure. Thus, one of ordinary skill in the art understands that the disclosure may be embodied in many different forms.

The present disclosure relates to a respiratory muscle strengthening device, in which an inhalation start signal is generated correspondingly at an inhalation start time when a patient inhales air or an exhalation start signal is generated correspondingly at an exhalation start time when the patient exhales air through a spontaneous breathing signal of the patent or an artificial respirator, an electric signal according to the inhalation start signal or the exhalation start signal is transmitted to an electric muscle stimulator via a communication unit, a muscle pad installed on respiratory muscles enables smooth breathing motion by stimulating the respiratory muscles based on a signal transmitted from the electric muscle stimulator, and a receptor pad is further provided to the respiratory muscles such that the receptor pad detects a state (muscle contraction and relaxation movement degrees, movement time, or the like) of the respiratory muscles to determine normal application of electric stimulation via the state of the respiratory muscles detected through the receptor pad and output an alarm when a normal range is exceeded, thereby securing reliability of a device, and will now described with reference to drawings.

A respiratory muscle strengthening device according to an embodiment of the present disclosure includes a respiration detecting unit 10, an electric muscle stimulator 20, a receptor pad 30, and an alarm unit 40, and first, an inhalation start signal is generated correspondingly at an inhalation start time when a patient inhales air and an exhalation start signal is generated correspondingly at an exhalation start time when the patient exhales air, wherein the inhalation start signal or the exhalation start signal transmitted to the electric muscle stimulator 20 is generated according to spontaneous breathing of the patient or respiration via an artificial respirator and is generated by the respiration detecting unit 10 for detecting inhalation or exhalation from a face of the patient.

The respiration detecting unit 10 generates the inhalation start signal correspondingly at the inhalation start time when the patient inhales air or generates the exhalation start signal correspondingly at the exhalation start time when the patient exhales air, and transmits the inhalation start signal or the exhalation start signal to the electric muscle stimulator 20.

Referring to the respiration detecting unit 10 according to an embodiment of the present disclosure in detail, the respiration detecting unit 10 includes an inhalation start signal generating unit 11 that generates the inhalation start signal by determining the inhalation start time when the patient inhales air, an exhalation start signal generating unit 12 that generates the exhalation start signal by determining the exhalation start time when the patient exhales air, and a communication unit 13 that converts the inhalation start signal generated by the inhalation start signal generating unit 11 or the exhalation start signal generated by the exhalation start signal generating unit 12 into a respiration stimulation signal, and transmits the respiration stimulation signal to the electric muscle stimulator 20.

Here, the respiration detecting unit 10 may be replaced by an artificial respirator, and the inhalation start signal generating unit 11 determines the inhalation start time when the patient inhales air (oxygen or the like) from the respiration detecting unit 10 (or detects a signal generated by the artificial respirator during inhalation of the patient), generates the inhalation start signal when the inhalation start time is determined, and applies the generated inhalation start signal (or the signal generated when inhalation is detected) to the communication unit 13.

Accordingly, the inhalation start signal generating unit 11 according to an embodiment of the present disclosure may pre-set the inhalation start signal operated during inhalation of the patient, generate the inhalation start signal according to a pre-set condition, and apply the inhalation start signal to the communication unit 13.

At this time, the inhalation start signal generating unit 11 according to an embodiment of the present disclosure may pre-set a ratio of inhalation to exhalation differently according to a condition of the patient, generate the inhalation start signal according to the pre-set ratio of inhalation to exhalation, and apply the inhalation start signal to the communication unit 13.

Also, the exhalation start signal generating unit 12 also determines the exhalation start time when the patient exhales air from the respiration detecting unit 10 (or detects a signal generated by the artificial respirator during exhalation of the patient), generates the exhalation start signal when the exhalation start time is determined, and applies the generated exhalation start signal (or the signal generated when exhalation is detected) to the communication unit 13.

Accordingly, the exhalation start signal generating unit 12 according to an embodiment of the present disclosure may also pre-set the exhalation start signal operated during exhalation of the patient, generate the exhalation start signal according to a pre-set condition, and apply the exhalation start signal to the communication unit 13.

At this time, the exhalation start signal generating unit 12 according to an embodiment of the present disclosure may pre-set a ratio of inhalation to exhalation differently according to a condition of the patient, generate the exhalation start signal according to the pre-set ratio of inhalation to exhalation, and apply the exhalation start signal to the communication unit 13.

The communication unit 13 includes a wired communication module (for example, a series communication module, a USB communication module, or the like), or a wireless communication module (for example, a short-range wireless communication module (for example, a Bluetooth communication module, an RF communication module, or the like)), converts (for example, encodes, or the like) the inhalation start signal (or the signal generated when inhalation is detected) input from the inhalation start signal generating unit 11 or the exhalation start signal (or the signal generated when exhalation is detected) input from the exhalation start signal generating unit 12 into the respiration stimulation signal, and transmits the respiration stimulation signal to the electric muscle stimulator 20 via wires or wirelessly.

In addition, the respiration detecting unit 10 according to an embodiment of the present disclosure further includes an inhalation exhalation ratio setting unit 14, wherein the inhalation exhalation ratio setting unit 14 pre-sets the ratio of inhalation to exhalation according to the condition of the patient and transmits information about the pre-set ratio of inhalation to exhalation to the electric muscle stimulator 20 through the communication unit 13.

At this time, the communication unit 13 converts the information about the ratio of inhalation to exhalation input from the inhalation exhalation ratio setting unit 14 into a ratio information transmission signal, and transmits the ratio information transmission signal to the electric muscle stimulator 20 via wires or wirelessly.

Also, the electric muscle stimulator 20 is installed on the respiratory muscles of the patient and stimulates the respiratory muscles based on the inhalation start signal or the exhalation start signal, and stimulates corresponding respiratory muscles upon receiving the inhalation start signal or the exhalation start signal from the respiration detecting unit 10.

The electric muscle stimulator 20 according to an embodiment of the present disclosure is described in detail with reference to FIGS. 3 and 4. The electric muscle stimulator 20 includes a communication unit 21, an operation control unit 22, a memory unit 23, and a plurality of electric stimulation pads 24 and 25. Here, the electric stimulation pads 24 and 25 may be classified into inhalation muscle pads 24 and exhalation muscle pads 25.

First, the communication unit 21 inverse-converts the respiration stimulation signal transmitted from the respiration detecting unit 10 into the inhalation start signal or the exhalation start signal, includes a wired communication module (for example, a series communication module, a USB communication module, or the like) or a wireless communication module (for example, a short-range wireless communication module (for example, a Bluetooth communication module, an RF communication module, or the like)), inverse-converts (for example, decodes or the like) the respiration stimulation signal into the inhalation start signal (or the signal generated when inhalation is detected) or the exhalation start signal (or the signal generated when exhalation is detected) upon receiving the respiration stimulation signal from the respiration detecting unit 10 via wires or wirelessly, and applies the inhalation start signal (or the signal generated when inhalation is detected) or the exhalation start signal (or the signal generated when exhalation is detected) to the operation control unit 22.

Accordingly, the communication unit 21 according to an embodiment of the present disclosure receives the ratio information transmission signal from the respiration detecting unit 10 via wires or wirelessly, inverse-converts the ratio information transmission signal into the information about the ratio of inhalation to exhalation, and applies the information about the ratio of inhalation to exhalation to the operation control unit 22.

Also, the operation control unit 22 generates a first driving control signal or a second driving control signal correspondingly to the inhalation start signal or the exhalation start signal obtained by the communication unit 21.

Also, the operation control unit 22 according to an embodiment of the present disclosure includes the memory 23 storing a program and data necessary for driving control of the operation control unit 22.

When the information about the ratio of inhalation to exhalation is input from the communication unit 21, the operation control unit 22 according to an embodiment of the present disclosure pre-sets electric stimulating times of corresponding inhalation muscles and exhalation muscles in the memory unit 23, and generates the first driving control signal for operating the inhalation muscles by an inhalation muscle electric stimulating time when the inhalation start signal is input from the communication unit 21 and generate the second driving control signal for operating the exhalation muscles by an exhalation muscle electric stimulating time when the exhalation start signal is input from the communication unit 21.

In detail, the operation control unit 22 according to the present disclosure controls operations of (i.e., operates) the corresponding electric stimulation pads 24 or 25 according to the inhalation start time (or the signal generated when inhalation is detected) or the exhalation start time (or the signal generated when exhalation is detected) input from the communication unit 21.

For example, when the inhalation start signal (or the signal generated when inhalation is detected) or the exhalation start signal (or the signal generated when exhalation is detected) is input from the communication unit 21, the operation control unit 22 may control operations of (i.e., operate) the corresponding electric stimulation pads 24 or 25 in synchronization with the input inhalation start signal (or the signal generated when inhalation is detected) or the input exhalation start signal (or the signal generated when exhalation is detected).

Here, when the inhalation start signal (or the signal generated when inhalation is detected) is input from the communication unit 21, the operation control unit 22 may generate the first driving control signals corresponding to the input inhalation start signal (or the signal generated when inhalation is detected) and apply the first driving control signals respectively to corresponding inhalation muscle pads 24, and when the exhalation start signal (or the signal generated when exhalation is detected) is input from the communication unit 21, the operation control unit 22 may generate the second driving control signals corresponding to the input exhalation start signal (or the signal generated when exhalation is detected) and apply the second driving control signals respectively to corresponding exhalation muscle pads 25.

Also, when the information about the ratio of inhalation to exhalation is input from the communication unit 21, the operation control unit 22 may pre-set the electric stimulating times of the inhalation muscles and the exhalation muscles corresponding to the input information about the ratio of inhalation to exhalation in the memory unit 23. For example, the operation control unit 22 may contract the respiratory muscles according to a condition pre-set in the memory unit 23, and in other words, when the inhalation start signal (or the signal generated when inhalation is detected) is input from the communication unit 21, the first driving control signals for operating the inhalation muscles by the inhalation muscle electric stimulating time pre-set in the memory unit 23 may be generated, and when the exhalation start signal (or the signal generated when exhalation is detected) is input from the communication unit 21, the second driving control signals for operating the exhalation muscles by the exhalation muscle electric stimulating time pre-set in the memory unit 23 may be generated.

The electric stimulation pads 24 and 25 are attached to and installed on the respiratory muscles of the patient, respectively, and stimulate the respiratory muscles by operating according to driving control of the operation control unit 22, respectively.

Here, the electric stimulation pads 24 and 25 according to an embodiment of the present disclosure are classified into the inhalation muscle pads 24 and the exhalation muscle pads 25, wherein the inhalation muscle pads 24 are pre-attached to the respiratory muscles (phren) of the patient and operate according to the first driving control signal input from the operation control unit 22 to stimulate (contract) the corresponding inhalation muscles.

Also, the exhalation muscle pads 25 are pre-attached to the exhalation muscles (abdominal muscles) among the respiratory muscles of the patient and operate according to the second driving control signal input from the operation control unit 22 to stimulate (contract) the corresponding exhalation muscles.

Here, in an embodiment of the present disclosure, the inhalation muscles and the exhalation muscles to which the inhalation muscles pads 24 and exhalation muscle pads 25 are attached are described limitedly to the phren and the abdominal muscles, respectively, but the inhalation muscle pads 24 may be attached not only to the phren, but also to large chest muscles, small chest muscles, trapezius muscles, erector spine muscles, or the like, and the exhalation muscle pads 25 may be attached to rectus abdominis muscles, external oblique abdominal muscles, internal oblique abdominal muscles, muscle transverses abdominis, or the like, as long as strain is not imposed on the patient's heart considering the condition of the patient.

The respiratory muscle strengthening device according to an embodiment of the present disclosure includes the receptor pad 30 that is installed on the respiratory muscles of the patient and detects a state (muscle contraction and relaxation degrees, movement time, or the like) of the respiratory muscles based on the inhalation start signal or the exhalation start signal of the respiration detecting unit 10 or artificial respirator electrically connected thereto.

Here, the receptor pad 30 detects contraction and relaxation degrees and times of the respiratory muscles, and is electrically connected to the operation control unit 22 of the electric muscle stimulator 20 to detect and transmit the state muscle contraction and relaxation degrees, movement time, or the like) of the respiratory muscles to the operation control unit 22 in real-time.

Figure 3:
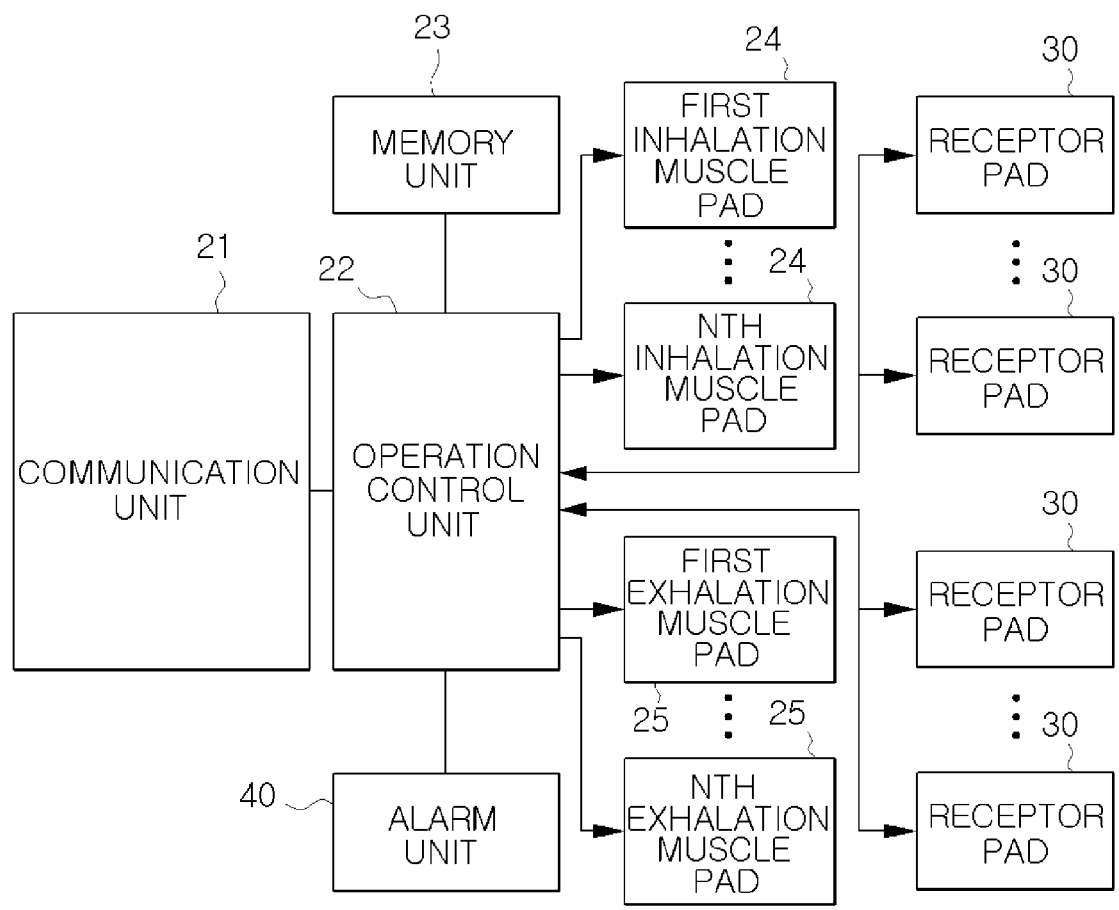
FIG. 3 is an exemplary diagram of an electric stimulator according to an embodiment of the present disclosure.

Also, as shown in FIG. 3, the receptor pad 30 may be provided separately from the inhalation muscle pads 24 or the exhalation muscle pads 25, and the receptor pad 30 provided separately from the inhalation muscle pads 24 or the exhalation muscle pads 25 may be attached around each of the inhalation muscle pads 24 or exhalation muscle pads 25 to detect the contraction and relaxation degrees and movement times of the inhalation muscles or exhalation muscles.

Figure 4:
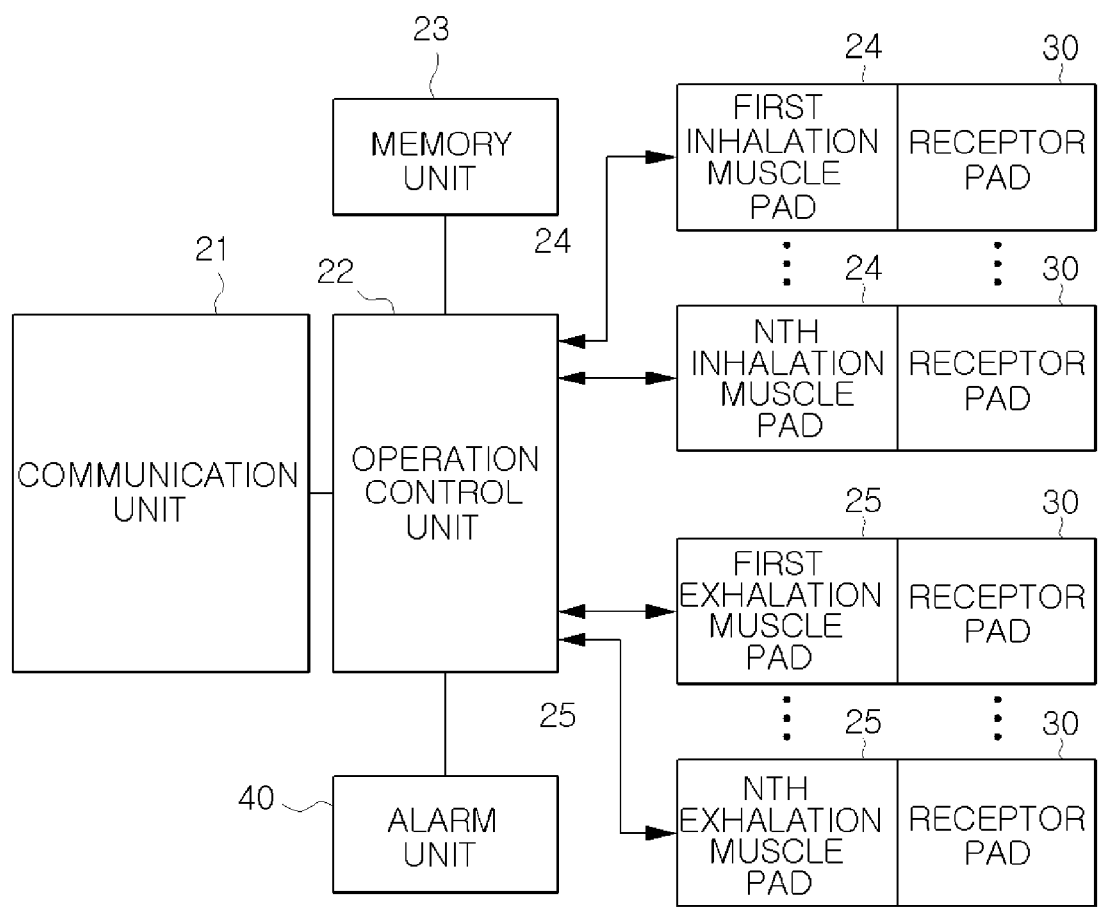
FIG. 4 is an exemplary diagram of an electric stimulator according to another embodiment of the present disclosure.

Also, as shown in FIG. 4, the receptor pad 30 may be provided integrally with the inhalation muscle pads 24 or the exhalation muscle pads 25 to detect the contraction and relaxation degrees and movement times of the inhalation muscles or exhalation muscles among the respiratory muscles.

The contraction and relaxation degrees and movement times of the respiratory muscles detected by the receptor pad 30 are transmitted to the operation control unit 22, and are compared with a stimulation degree of the first driving control signal or second driving control signal pre-set in the memory unit 23.

The contraction and relaxation degrees and movement times of the respiratory muscles detected by the receptor pad 30 are transmitted to the operation control unit 22.

The operation control unit 22 may compare the contraction and relaxation degrees of the respiratory muscles transmitted from the receptor pad 30 with contraction and relaxation degrees of the respiratory muscles corresponding to stimulation of the first driving signal or second driving signal, and determine whether electric stimulation is normally applied.

Here, the electric stimulation according to the first driving control signal or second driving control signal pre-set in the memory unit 23 and the contraction and relaxation degrees of the respiratory muscles detected by the receptor pad 30 are compared, and when it is determined that the electric stimulation is outside a normal range, the operation control unit 22 outputs an alarm by driving the alarm unit 40 to notify an operator that abnormal electric stimulation is currently detected such that a consequent action is taken.

Accordingly, the respiratory muscle strengthening device according to an embodiment of the present disclosure may use respiratory muscles while simultaneously curing a respiratory disease by continuously using the respiratory muscles even while an artificial respirator is used, and accordingly, manpower, time, and economical costs of additional treatment for respiratory muscle strengthening exercise performed again after the respiratory disease is medically cured may be reduced, and not only the respiratory muscles are strengthened, but also early respirator weaning is induced. Also, by performing strengthening exercise of the respiratory muscles through a pad attached to the respiratory muscles by using an electric neuromuscle stimulator, a method of use is simple, an additional space or equipment is not required, synergy is generated with respect to respiration, and the respiratory muscles are continuously strengthened, and thus the respirator weaning may be advanced.

Also, by further providing a receptor pad to the respiratory muscles, a degree of electric stimulation applied to the respiratory muscles may be objectively determined, and a first driving control signal or a second driving control signal applied to the inhalation muscle pads 24 or exhalation muscle pads 25 may be corrected considering a movement (contraction or relaxation) degree of the respiratory muscles, which is actually applied, and thus reliability of a device may be secured.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

The invention claimed is:

1. A respiratory muscle strengthening device comprising:
   a respiration detecting unit configured to generate an inhalation start signal correspondingly at an inhalation start time when a patient inhales air or generating an exhalation start signal correspondingly at an exhalation start time when the patient exhales air;
   an electric muscle stimulator capable of being attached to respiratory muscles of a patient and configured to stimulate the respiratory muscles based on the inhalation start signal or the exhalation start signal,
   wherein the respiration detecting unit configured to transmit the inhalation start signal or the exhalation start signal to the electric muscle stimulator;
   a receptor pad capable of being attached to the respiratory muscles of the patient and configured to detect contraction and relaxation degrees and times of the respiratory muscles;
   a communication unit for converting either spontaneous breathing of the patient or a respiratory stimulation signal applied from an outside to the inhalation start signal or the exhalation start signal; and
   an operation control unit configured to generate a first driving control signal or a second driving control signal correspondingly to the inhalation start signal or the exhalation start signal obtained by the communication unit.

2. The respiratory muscle strengthening device of claim 1, wherein the operation control unit is configured to pre-sets an electric stimulating time of the respiratory muscles corresponding to the inhalation start signal or the exhalation start signal, wherein the drive control signals contract inhalation muscles when the inhalation start signal is received, and contracts exhalation muscles when the exhalation start signal is received.

3. The respiratory muscle strengthening device of claim 1, wherein the electric muscle stimulator comprises:
   a memory unit for storing a program and data necessary for driving control of the operation control unit;
   a plurality of inhalation muscle pads for attaching respectively to inhalation muscles among the respiratory muscles of the patient and stimulating a corresponding inhalation muscle according to the first driving control signal generated by the operation control unit; and
   a plurality of exhalation muscle pads for attaching respectively to exhalation muscles among the respiratory muscles of the patient and stimulating a corresponding exhalation muscle according to the second driving control signal generated by the operation control unit.

4. The respiratory muscle strengthening device of claim 3, wherein the receptor pad is provided separately from each of the plurality of inhalation muscle pads or the plurality of exhalation muscle pads to detect a motion degree of the respiratory muscles.

5. The respiratory muscle strengthening device of claim 3, wherein the receptor pad is capable of being attached to the inhalation muscles or the exhalation muscles and is provided integrated with the plurality of inhalation muscle pads or the plurality of exhalation muscle pads to detect a motion degree of the respiratory muscles.

6. The respiratory muscle strengthening device of claim 3, wherein the operation control unit determines electric stimulation output through the plurality of inhalation muscle pads or the plurality of exhalation muscle pads, and also determines whether the electric stimulation is within a pre-fixed range applied via the contraction and relaxation degrees and times of the respiratory muscles detected through the receptor pad.

7. The respiratory muscle strengthening device of claim 6, further comprising an alarm unit configured to generate alarm sound to a user when the operation control unit determines that the electric stimulation is outside the pre-fixed range.

* * * * *